(12) United States Patent
Inagaki et al.

(10) Patent No.: US 12,142,099 B2
(45) Date of Patent: Nov. 12, 2024

(54) INFORMATION PROCESSING SYSTEM, INFORMATION PROCESSING METHOD AND COMPUTER PROGRAM

(71) Applicants: NEC Corporation, Tokyo (JP); NEC Platforms, Ltd., Kawasaki (JP)

(72) Inventors: Fumiyuki Inagaki, Kanagawa (JP); Fumi Irie, Tokyo (JP)

(73) Assignees: NEC CORPORATION, Tokyo (JP); NEC Platforms, Ltd., Kanagawa (JP)

( * ) Notice: Subject to any disclaimer, the term of this patent is extended or adjusted under 35 U.S.C. 154(b) by 0 days.

(21) Appl. No.: 17/639,961

(22) PCT Filed: Mar. 25, 2021

(86) PCT No.: PCT/JP2021/012601
§ 371 (c)(1),
(2) Date: Mar. 3, 2022

(87) PCT Pub. No.: WO2022/201443
PCT Pub. Date: Sep. 29, 2022

(65) Prior Publication Data
US 2024/0046726 A1 Feb. 8, 2024

(51) Int. Cl.
*A61B 5/00* (2006.01)
*G01N 35/00* (2006.01)
(Continued)

(52) U.S. Cl.
CPC ....... *G07C 9/257* (2020.01); *G01N 35/00871* (2013.01); *G07C 9/00658* (2013.01); *G16H 50/30* (2018.01)

(58) Field of Classification Search
CPC .. G06Q 50/265; G06Q 30/0185; G06Q 50/01; G06Q 10/02; G06Q 10/10;
(Continued)

(56) References Cited

U.S. PATENT DOCUMENTS 11,054,411 B2 * 7/2021 Linssen .............. G01N 15/1459
11,151,820 B1 * 10/2021 Klein .................. G06Q 50/265
(Continued)

FOREIGN PATENT DOCUMENTS

JP     2005-135310 A    5/2005
JP     2011-002407 A    1/2011
(Continued)

OTHER PUBLICATIONS

International Search Report for PCT Application No. PCT/JP2021/012601, mailed on Apr. 27, 2021.
(Continued)

*Primary Examiner* — Dionne Pendleton
(74) *Attorney, Agent, or Firm* — Sughrue Mion, PLLC

(57) ABSTRACT

An information processing system (10) comprises: a first acquiring means (210) for acquiring a first information relating to performance of a specific inspection; a second acquiring means (220) for acquiring a second information for determining that whether or not a user is a person who has gotten the specific inspection; a determining means (300) for performing a determination that whether or not the user has gotten the specific inspection on the basis of the first information and the second information; and an output means (400) for performing an output according to a result of the determination. According to such the information processing system, it is possible to appropriately process information relating to a specific inspection.

15 Claims, 18 Drawing Sheets

(51) Int. Cl.
*G07C 9/00* (2020.01)
*G07C 9/25* (2020.01)
*G16H 50/30* (2018.01)

(58) Field of Classification Search
CPC .. G06Q 10/103; G06Q 10/105; G06Q 10/107; G06Q 20/047; G06Q 20/4014; G06Q 2230/00; G06Q 2240/00; G06Q 30/018; G06Q 50/205; G06Q 50/26; G07C 9/00; G07C 9/00658; G07C 9/25; G07C 9/257; G07C 9/27; G07C 9/10; G07C 9/37; G07C 13/00; G07C 9/00563; G07C 9/15; G07C 9/20; G07C 9/253; G07C 9/32; G07C 9/38; G06K 19/00; G06K 19/06037; G06K 7/1417; G06K 19/06112; G06K 19/0614; G06K 19/06168; G06K 7/10297; G06K 7/1095; G06K 7/1413; G06F 21/30; G06F 21/6245; G06F 21/31; G06F 21/33; G06F 21/32; G06F 21/36; G06F 21/45; G06F 21/602; G06F 21/62; G16H 10/60; G16H 10/40; G16H 50/80; G16H 15/00; G16H 10/20; G16H 10/65; G16H 40/20; G16H 40/67; G16H 50/30; G16H 50/20; G16H 80/00; G16H 20/13; G16H 30/40; G16H 40/63; G16H 50/50; A61B 5/0022; A61B 2503/12; A61B 2562/08; A61B 5/01; A61B 5/055; A61B 5/0816; A61B 5/0823; A61B 5/1172; A61B 5/4011; A61B 5/4017; A61B 5/4833; A61B 5/746; A61B 5/7465; A61B 6/032; A61B 8/08; A61B 8/48; A61B 8/5207; G06V 30/10; G06V 30/414; H04L 63/08; H04L 63/0861; H04L 2209/80; H04L 63/067; H04L 63/0838; H04L 63/101; H04L 9/0816; H04L 9/321; H04W 12/069; H04W 12/77; H04W 12/63; H04W 12/64; H04W 4/021; H04W 4/029; Y02A 90/10; A61L 2/0088; A61L 2/26; A61L 2202/15; C12Q 1/04; G01N 2021/6421; G01N 21/6428; G07F 17/0092; G08B 21/245

See application file for complete search history.

(56) References Cited

U.S. PATENT DOCUMENTS

| 2015/0112704 | A1* | 4/2015 | Braun | G06Q 10/10 |
| | | | | 705/2 |
| 2015/0359477 | A1* | 12/2015 | Ramachandran | A61B 5/486 |
| | | | | 434/362 |
| 2020/0393159 | A1 | 12/2020 | Takayanagi | |
| 2021/0350648 | A1* | 11/2021 | Lodha | G06Q 20/40145 |

FOREIGN PATENT DOCUMENTS

| JP | 2018-128970 A | 8/2018 |
| JP | 2019-152993 A | 9/2019 |
| JP | 2021-007000 A | 1/2021 |
| JP | 2021-043634 A | 3/2021 |
| WO | 2019/239812 A1 | 12/2019 |

OTHER PUBLICATIONS

ANA Holdings Inc. press release, "We will carry out a demonstration experiment of 'IATA Travel Pass', digital certificate app for new coronavirus test results and vaccination records", [online], Mar. 10, 2021, [retrieval date: Apr. 20, 2021], internet<URL:https://www.anahd.co.jp/group/pr/202103/20210310-3.html> p. 1-2.

* cited by examiner

FIG. 11

|  | Name of inspection | Inspection result | The date, in which inspection was performed |
|---|---|---|---|
| Inspection (1) | Vaccination | Inoculation completed | 2021. ○. ○ |
| Inspection (2) | PCR inspection | Negative | 2021. □. □ |

INFORMATION PROCESSING SYSTEM, INFORMATION PROCESSING METHOD AND COMPUTER PROGRAM

This application is a National Stage Entry of PCT/JP2021/012601 filed on Mar. 25, 2021, the contents of all of which are incorporated herein by reference, in their entirety.

TECHNICAL FIELD

This disclosure relates to technical fields of an information processing system, an information processing method and a computer program for processing information relating to a specific inspection.

BACKGROUND ART

It is known that a system manages information relating to inspection results as this type of system. For example, Patent Literature 1 discloses a technique for determining that whether or not a user is permitted to board an airplane on the basis of inspection results registered in a server when the user boards the airplane.

As other related arts, for example, Patent Literature 2 discloses using a two-dimensional code, which is described in a digital ticket or the like, and a face authentication together. Patent Literature 3 discloses performing a face authentication by using face data read from a two-dimensional code.

CITATION LIST

Patent Literature

Patent Literature 1: Japanese Patent Application Laid Open No. 2021-007000
Patent Literature 2: Japanese Patent Application Laid Open No. 2018-128970
Patent Literature 3: Japanese Patent Application Laid Open No. 2005-135310

SUMMARY

Technical Problem

This disclosure aims to improve techniques disclosed in the prior art literature.

Solution to Problem

One aspect of the information processing system of this disclosure is provided with: a first acquiring means for acquiring a first information relating to performance of a specific inspection; a second acquiring means for acquiring a second information for determining that whether or not a user is a person who has gotten the specific inspection; a determining means for performing a determination that whether or not the user has gotten the specific inspection on the basis of the first information and the second information; and an output means for performing an output according to a result of the determination.

One aspect of the information processing method of this disclosure comprises: acquiring a first information relating to performance of a specific inspection; acquiring a second information for determining the whether or not a user is a person who has gotten the specific inspection; determining that whether or not the user has gotten the specific inspection on the basis of the first information and the second information; and performing an output according to the result of the determination.

One aspect of a computer program of this disclosure causes a computer to: acquiring a first information relating to performance of a specific inspection; acquiring a second information for determining the whether or not a user is a person who has gotten the specific inspection; determining that whether or not the user has gotten the specific inspection on the basis of the first information and the second information; and performing an output according to the result of the determination.

BRIEF DESCRIPTION OF DRAWINGS

FIG. 11 is a table showing an example of a first information acquired by an information processing system of a fifth embodiment.

DESCRIPTION OF EMBODIMENTS

Hereinafter, embodiments of an information processing system, an information processing method and a computer program will be described referring to drawings.

First Embodiment

An information processing system of a first embodiment will be described referring to FIGS. 1 to 3.
(Hardware Configuration)

First, a hardware configuration of the information processing system 10 of the first embodiment will be described referring to FIG. 1. FIG. 1 is a block diagram showing the hardware configuration of the information processing system of the first embodiment.

Figure 1:
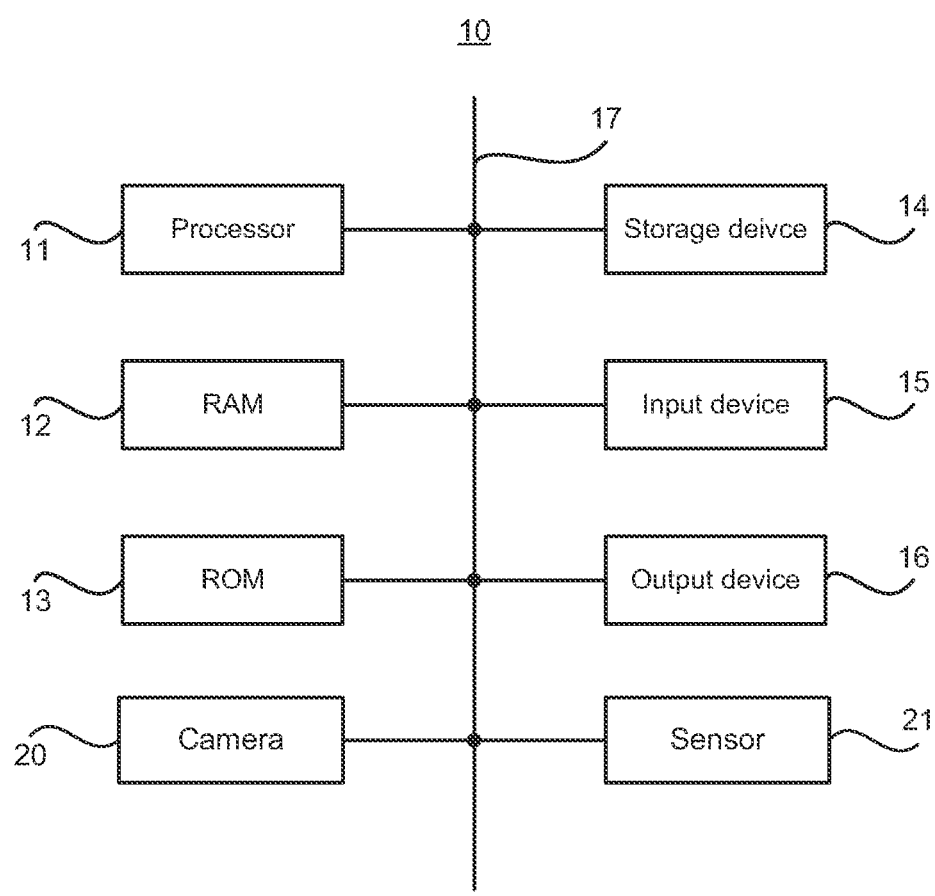
FIG. 1 is a block diagram showing a hardware configuration of an information processing system of a first embodiment.

As shown in FIG. 1, the information processing system 10 of the first embodiment includes the processor 11, the RAM (Random Access Memory) 12, the ROM (Read Only Memory) 13 and the storage device 14. The information processing system 10 may further include the input device 15 and the output device 16. The information processing system 10 may also include the camera 20 and the sensor 21. The processor 11, the RAM 12, the ROM 13, the storage device 14, the input device 15, the output device 16, the camera 20 and the sensor 21 are connected via the data bus 17.

The processor 11 reads computer programs. For example, the processor 11 is configured to read a computer program stored in at least one of the RAM 12, the ROM 13 and the storage device 14. Alternatively, the processor 11 may read a computer program stored in a computer-readable recording medium by using a recording medium reading apparatus not shown. The processor 11 may acquire (i.e., read) a computer program from an apparatus, which is not shown, and which is located outside the information processing system 10, via a network interface. The processor 11 controls the RAM 12, the storage device 14, the input device 15 and the output device 16 by executing the read computer program. In particular, in this embodiment, when the processor 11 executes the read computer program, function blocks for processing information related to a specific inspection are realized in the processor 11. a CPU (Central Processing Unit), a GPU (Graphics Processing Unit), a FPGA (field-programmable gate array), a DSP (Demand-Side Platform) and an ASIC (Application Specific Integrated Circuit) are listed as examples of the processor 11. The processor 11 may use one of the above described examples, or may use a plurality of the above described examples in parallel.

The RAM 12 temporarily stores computer programs executed by the processor 11. The RAM 12 temporarily stores data, which are used by the processor 11 when the processor 11 is executing computer programs. The RAM 12 may be D-RAM (Dynamic RAM), for example.

The ROM 13 stores computer programs executed by the processor 11. The ROM 13 may store other fixed data. The ROM 13 may be P-ROM (Programmable ROM), for example.

The storage device 14 stores data that the information processing system 10 stores for a long period of time. The storage device 14 may function as a temporary storage device of the processor 11. The storage device 14 may include at least one of a hard disk apparatus, a magneto-optical disk apparatus, an SSD (Solid State Drive) and a disk array apparatus, for example.

The input device 15 is a device which receives input instructions from a user of the information processing system 10. The input device 15 may include at least one of a keyboard, a mouse and a touch panel, for example. The input device 15 may be a dedicated controller (operating terminal). The input device 15 may also include user-owned terminals (e.g., a smartphone, a tablet terminal, etc.). The input device 15 may be a device capable of audio input including a microphone, for example.

The output device 16 is a device, which outputs information relating to the information processing system 10 to the outside. For example, the output device 16 may be a display apparatus (e.g., a display) capable of displaying information relating to the information processing system 10. The display apparatus here may be a TV monitor, a PC monitor, a monitor or a smartphone, a monitor of a tablet terminal, or a monitor of other portable terminal. In addition, the display apparatus may be a large monitor or a digital signage installed in various facilities such as stores. The output device 16 may be a device which outputs information in a format other than an image. For example, the output device 16 may be a speaker for outputting audio information relating to the information processing system 10.

(Functional Configuration)

Next, a functional configuration of the information processing system 10 of the first embodiment will be described referring to FIG. 2. FIG. 2 is a block diagram showing the functional configuration of the information processing system of the first embodiment.

Figure 2:
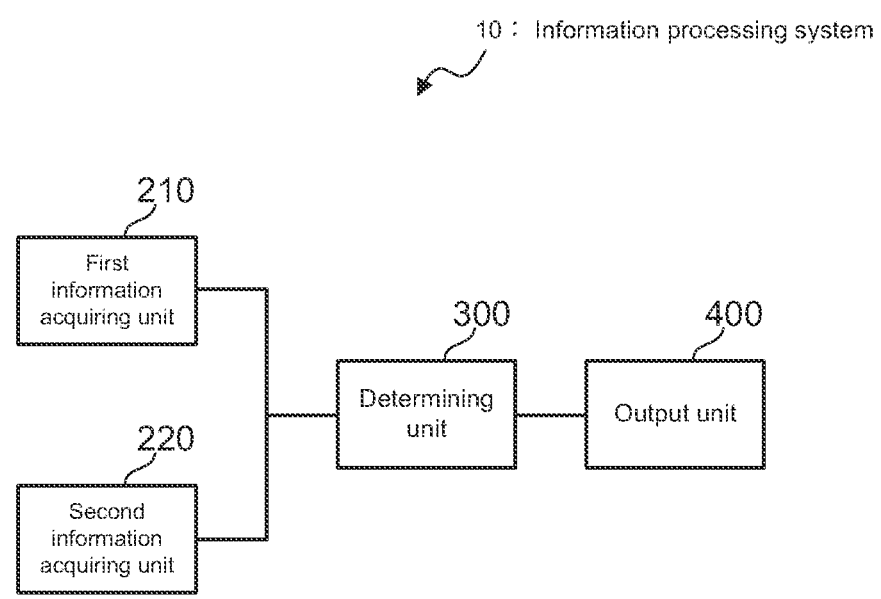
FIG. 2 is a block diagram showing a functional configuration of the information processing system of the first embodiment.

As shown in FIG. 2, the information processing system 10 of the first embodiment is configured to include the first information acquiring unit 210, the second information acquiring unit 220, the determining unit 300 and the output unit 400 as processing blocks for realizing functions. Each of the first information acquiring unit 210, the second information acquiring unit 220, the determining unit 300 and the output unit 400 may be realized by the above-described processor 11 or the like, for example.

The first information acquiring unit 210 is configured to be able to acquire a first information. The first information is information relating to performance of a specific inspection, which may include, for example, information indicating whether or not a person has gotten an inspection, and information indicating date and time in which a person has gotten an inspection. Here, the "specific inspection" may include various inspections relating to pathogens, as well as inoculations of vaccines or the like. The first information may also include information identifying a user, who has gotten the specific inspection. The first information may be information associated with "Common Pass", which is a digital certificate for sharing a result of a PCR-test, etc. The first information acquiring unit 210 may acquire the first information from a two-dimensional code possessed by a user, for example. This two-dimensional code may be printed on a paper, or may be electrically displayed on a smartphone or the like.

The second information acquiring unit 220 is configured to be able to acquire a second information. The second information is information for determining that whether or not a user is a person who has gotten the specific inspection. The second information may include information specifying the user whose first information is acquired (for example, the user who has shown the two-dimensional code when the first information has been acquired). The second information may include, for example, an image of the user imaged by a camera, or may include unique information acquired from a terminal possessed by the user. The second information may be information, which can be determined that whether or not the user is a person who has gotten the specific inspection by comparing with the first information.

The determining unit 300 is configured to be able to determine that whether or not the user (i.e., the user whose first information has been acquired) has gotten the specific inspection on the basis of the first information and the second information. In other words, the determining unit 300 is configured to be able to determine that whether or not a user, who has not gotten the specific inspection actually, pretends to be other user, who has gotten the specific inspection. The determining unit 300 is configured to be able to determine that whether or not information included in the first information (i.e., information relating to a user, who has gotten the specific inspection) matches information included in the second information (i.e., information relating to a user who actually uses the system), for example.

The output unit 400 is configured to be able to perform output according to a determination result of the determining unit 300. The output unit 400 may output the determination result as it is. For example, the output unit 400 may display the determination result on a display, may acoustically output the determination result by using a speaker or the like. Alternatively, the output unit 400 may output information, which is different from the determination result determined according to the determination result. For example, the output unit 400 may perform output for allowing the user to pass according to the determination result (specifically, allowing a user, who has gotten the specific inspection, to pass and prohibiting a user, who has not gotten the specific inspection, to pass). In this case, the output unit 400 may perform output that controls open/close of a gate, which is passed through by the user.

(Flow of Operation)

Next, flow of the operation of the information processing system 10 of the first embodiment will be described referring to FIG. 3. FIG. 3 is a flowchart showing the flow of the operation of the information processing system of the first embodiment.

Figure 3:
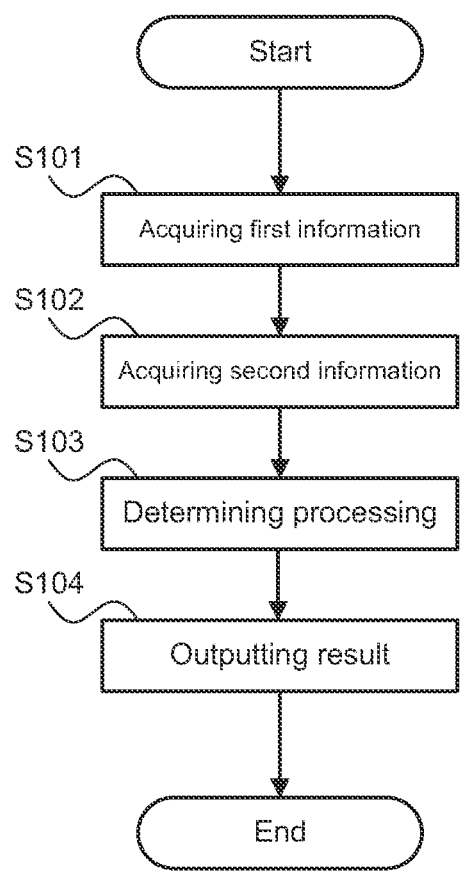
FIG. 3 is a flowchart showing flow of an operation of the information processing system of the first embodiment.

As shown in FIG. 3, when the information processing system 10 of the first embodiment operates, first, the first information acquiring unit 210 acquires the first information (step S101). Further, the second information acquiring unit 220 acquires the second information (step S102). The step S101 and the step S102 may be performed back and forth to each other, or may be performed in parallel at the same time.

Then, the determining unit 300 performs the determination that whether or not the user has gotten the specific inspection on the basis of the first information and the second information (step S103). Then, the output unit 400 performs output according to the determination result of the determining unit 300 (step S104).

(Technical Effects)

Next, technical effects obtained by the information processing system 10 of the first embodiment will be described.

As described referring to FIGS. 1 to 3, in the information processing system 10 of the first embodiment, it is determined that whether or not the user has gotten the specific inspection on the basis of the first information and the second information. In this way, for example, it is possible to determine "spoofing" by an unauthorized user. Specifically, it is possible to appropriately determine that whether or not a user, who has not gotten the specific inspection actually, pretends to be other user, who has gotten the specific inspection.

Concrete Application Examples

Here, a concrete application example of the information processing system 10 of the this embodiment will be described referring to FIGS. 3 and 4. In the following, an example will be described. Wherein the example is that the information processing system 10 of this embodiment is configured to be as an entry inspection system installed at an airport or the like, for example.

<Entire Configuration>

First, an entire configuration of the information processing system 10 applied to the entry inspection system will be described referring to FIG. 4. FIG. 4 is a conceptual diagram showing the concrete application example of the information processing system.

Figure 4:
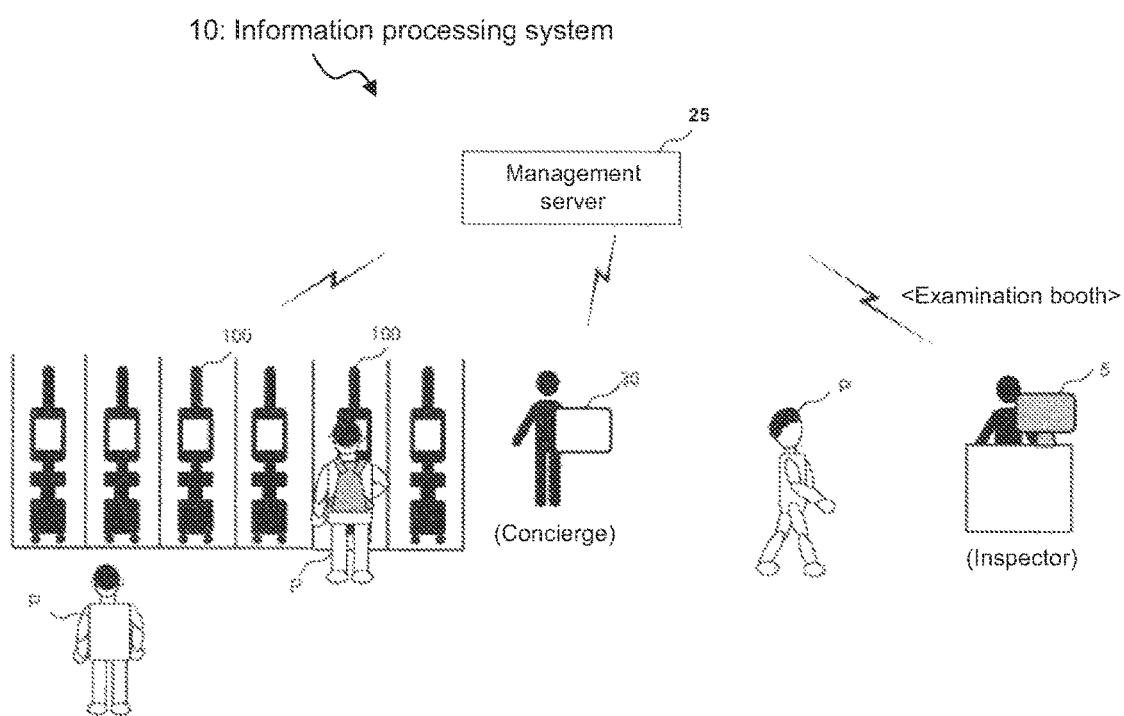
FIG. 4 is a conceptual diagram showing a concrete application example of the information processing system.

As shown in FIG. 4, entry examinations are basically carried out in two steps: obtaining personal identification information and performing entry inspections by inspectors. Specifically, when an entrant gets off an airplane and enters an entry inspection area, first, he/she provides the personal identification information by operating the operation terminal 100. Then, the entrant goes to an examination booth, in which inspectors are present, undertakes inspections performed by inspectors. When inspections performed by inspectors is completed, the entrant is admitted into a country.

The information processing system 10, which is the entry inspection system, includes the plurality of operation terminals 100, the management server 25, the tablet 30 and the PC 5. The operation terminal 100 is provided for acquiring personal identification information of the entrant P. The personal identification information may include a face image and fingerprint. The entrant P is not limited to a foreign national, but can be applied to all person who wish to admit into the country. Incidentally, the entrant P may be not only a human but also an animal such as a dog, a cat, a snake or the like. These entrants P are examples of "users". The information processing system 10 of this embodiment may be configured to be able to determine spoofing of the entrant P, who undertakes the entry inspection.

The concierge standbys near operation terminals 100 for perform management of operation terminals 100, and for performing support of operation of operation terminals 100. The concierge is assigned a predetermined number of operation terminals 100, that the concierge takes charge of. The concierge has the tablet 30, which is used in performing management of operation terminals 100 or the like. The tablet 30 is an example. Any terminal such as a PC or a smartphone may be used as long as the terminal apparatus, which can manage operation terminals 100. Incidentally, the concierge may be assigned an assistant (supporter) to perform assistive work.

At the examination booth, the inspector standbys, and examines the entrant P, who has provided the personal identification information. The PC 5, which is used by the inspector, is installed at the examination booth. The inspector performs examination by displaying the personal identification information or the like on the PC 5. Incidentally, although FIG. 4 shows only one examination booth for convenience, in practice a plurality of examination booths are installed.

The management server 25 manages and controls operation terminals 100 and the tablet 30 via wireless communication. The management server 25 also communicates with the PC 5 used by the inspector by wire or wirelessly. Specifically, the operation terminal 100 transmits information, which is provided by the entrant P by operating the operation terminal 100, to the management server 25. The management server 25 stores the information acquired from the operation terminal 100, and transmits the information to the tablet 30 and the PC 5. The tablet 30 receives information indicating the operation state of the operation terminal 100 from the management server 25, and displays the information. Thus, the concierge can grasp the state of each of operation terminals 100 that are taken charge of by he/she.

The management server 25 further transmits the personal identification information, which is provided by the entrant P by operating the operation terminal 100, to the PC 5 of the examination booth. The inspector makes the PC 5 display the personal identification information of the entrant P received from the management server 25, and performs the examination by referring to the content of it. In the above-described example, operation terminals 100, the tablet 30 of the concierge and the PC 5 of the examination booth transmit and receive information through the management server 25. However, those may be configured to perform transmitting and receiving information directly between operation terminals 100 and the tablet 30, and between operation terminals 100 and the PC 5 of the examination booth without passing through the management server 25.

<Configuration of Operation Terminals>

Figure 5:
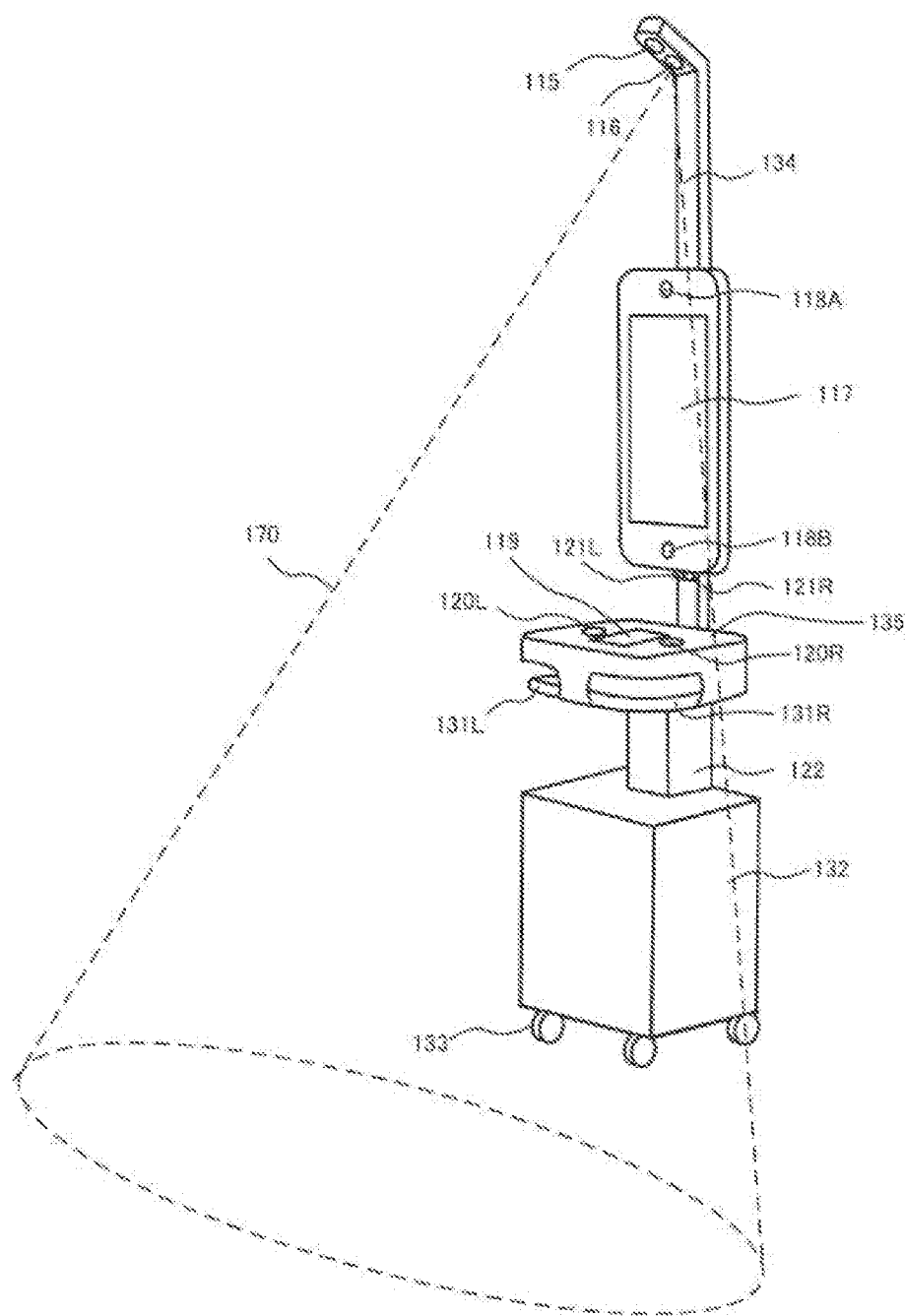
FIG. 5 is a perspective view showing a concrete configuration of an operation terminal.

Next, a concrete configuration of the operation terminal 100 in the above-described entry inspection system will be described with reference to FIG. 5. FIG. 5 is a perspective view showing the concrete configuration of the operation terminal.

As shown in FIG. 5, the operation terminal 100 includes the thermo-sensor 115, the surveillance camera 116, the touch panel 117, two face authentication cameras 118A and 118B, the passport reader 119, the pair of fingerprint scanners 120R and 120L, the pair of hand cameras 121R and 121L, the lifting mechanism 122, the pair of moving handles 131R and 131L, the base 132, the moving caster 133, the bar 134, and the table 135. In the following description, when it is not necessary to identify the elements composed of pairs, the subscripts are abbreviated. For example, when any one of fingerprint scanners 120R and 120R is specified, the "fingerprint scanner 120R", the "fingerprint scanner 120L" and the like are described, and when any one of fingerprint scanners is not specified, the "fingerprint scanner 120" is simply described.

The thermo-sensor 115 is provided at the top of the operation terminal 100 to detect proximity of the user to the operation terminal 100. Basically, in a condition in which the thermo-sensor 115 does not detect the user, the operation terminal 100 is in a standby (sleep) state. When the user stands in front of the thermo-sensor 115, the thermo-sensor 115 detects the user as a heat source and the operating terminal 100 is activated.

The surveillance camera 116, similarly to the thermo-sensor 115, is provided at the top of the operation terminal 100 to image a predetermined range in front of the operation terminal 100 from diagonally above. The surveillance camera 116 is used to image the behavior of the user in front of the operation terminal 100.

The touch panel 117 is provided at a position corresponding to an upper body of the user standing in front of the operation terminal 100 and is movable in the vertical direction along the bar 134. The touch panel 117 has functions as an input unit and a display unit when the user operates the operation terminal 100. The touch panel 117 may display guide information necessary when the user operates the operation terminal 100. In addition, when it is necessary for the user to make some selection with respect to the guide information, selection buttons may be displayed on the touch panel 117.

The face authentication camera 118A is provided at the upper end of the touch panel 117, and the face authentication camera 118B is provided at the lower end of it. Basically, the upper face authentication camera 118A is used to image face images of tall persons, and the lower face authentication camera 118B is used to image face images of short persons such as children. Thus, it is likely that an image (e.g., a face image on the front) suitable for the face authentication can be imaged by selecting the face authentication camera to be used in accordance with imaging targets. The upper face authentication camera 118A may image face images of short persons, and the lower face authentication camera 118B may image face images of tall persons. In addition, it is possible to obtain not only face images of the front face but also face images of various angles by using a plurality of face authentication cameras.

In the case where the touch panel 117 is movable in the vertical direction along the bar 134 as in this embodiment, one face authentication camera may be provided near the center in the vertical direction of the touch panel 117. Further, in the example of FIG. 5, the face authentication cameras 118A and 118B are respectively provided at the upper and the lower of the outside of the display area of the touch panel 117, but instead, a half mirror may be provided on the touch panel 117 and a face authentication camera may be provided at any position inside the half mirror. It is possible to image face images without making the user aware of the presence of the camera by providing the face authentication camera inside the half mirror in this way.

The table 135 is provided below the touch panel 117. The passport reader 119 and the pair of fingerprint scanners 120R and 120L are provided on the upper surface of the table 135. The passport reader 119 reads the recorded information via wireless communication from the IC chip in a passport placed on the passport reader 119. Specifically, the passport reader 119 reads from the passport matters of identification, such as nationality, name, date of birth and passport number, as well as the face image of the photographs attached to the application form of the passport (hereinafter collectively referred to as "passport information"). The fingerprint scanner 120 reads the fingerprints of index fingers of the left and right hand of the user. The fingerprint scanner 120R is for the right hand, and the fingerprint scanner 120L is for the left hand.

The lifting mechanism 122 moves the table 135 in the vertical direction. The lifting mechanism 122 allows the table 135 to be moved to a height that matches the height of the user, i.e., a height at which the user can easily place his or her fingers on fingerprint scanners 120R and 120L. Further, the lifting mechanism 122 moves the touch panel 117 along the bar 134. The mechanism for moving the touch panel 117 along the bar 134 may be any. The touch panel 117 may be raised and lowered by providing a rail on the front surface of the bar 135, fixing the touch panel 117 on a slider, which can vertically move in the rail, vertically moving the slider by the lifting mechanism 122, for example.

The pair of hand cameras 121R and 121L are provided above the table 135. Hand cameras 121R and 121L image a condition, in which a user places his/her passport on the passport reader 119, and a condition, in which left and right fingers of the user are placed on the fingerprint scanner 120, or the like. The hand camera 121R images the right hand side of the user, that is, the fingerprint scanner 120R side, and the hand camera 121L images the left hand side of the user, that is, the fingerprint scanner 120L side. The hand camera 121 may be provided at the lower end of the touch panel 117 and may be provided on the bar 134 at a position behind the touch panel 117.

The base 132 is a housing provided at the lower end of the operation terminal 100, the interior houses a removable battery or a spare battery or the like. The operating terminal 100 is powered by the removable battery so that it can be moved to a location without an electrical outlet for use. The moving caster 133 is provided below the base 132, and the pair of moving handles 131R and 131L are provided at the lower end of the table 135. A concierge and other workers can move the operation terminal 100 by holding the moving handle 131.

In embodiments hereinafter, a configuration, in which the first information and the second information are acquired in the operation terminal 100 described above, will be described as an example.

Second Embodiment

The information processing system 10 of the second embodiment will be described referring to FIGS. 6 and 7. The second embodiment is different from the first embodiment described above only in a part of configuration and operation, other part of the second embodiment may be the same as the first embodiment (see FIGS. 1 to 3). Therefore, in the following, the description of portions overlapping with the first embodiment already described are omitted.
(Functional Configuration)

First, a functional configuration of the information processing system 10 of the second embodiment will be described referring to FIG. 6. FIG. 6 is a block diagram showing the functional configuration of the information processing system of the second embodiment. Incidentally, in FIG. 6, the same reference numeral is given to an element, which is the same as the components shown in FIG. 2.

Figure 6:
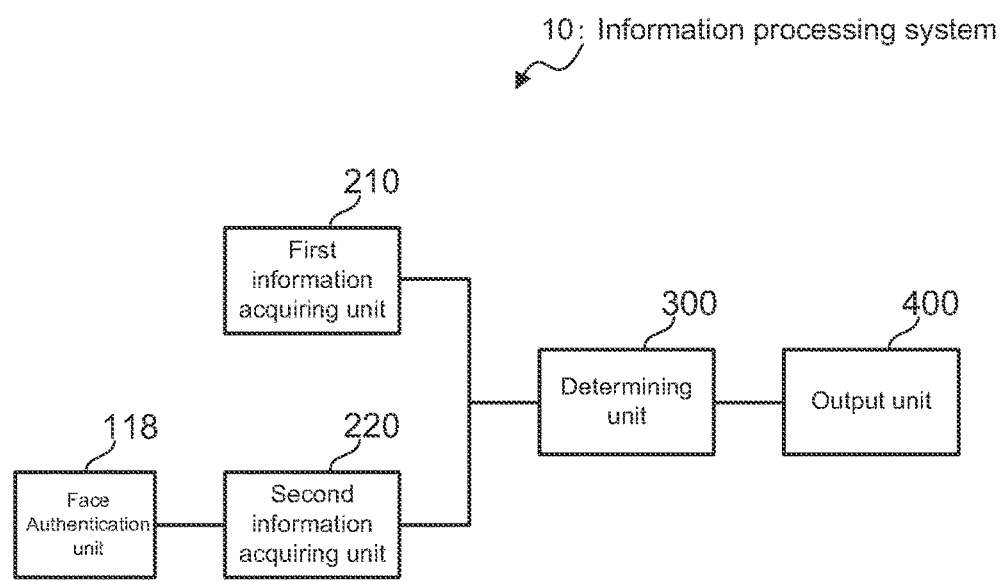
FIG. 6 is a block diagram showing a functional configuration of an information processing system of a second embodiment.

As shown in FIG. 6, the information processing system 10 of the second embodiment is configured to include the first information acquiring unit 210, the second information acquiring unit 220, the determining unit 300 and the output unit 400 as processing blocks for realizing the functions. In particular, the second information acquiring unit 220 of the second embodiment is configured to be able to acquire the second information by using the face authentication camera 118. Specifically, the second information acquiring unit 220 is configured to be able to acquire a face image of a user imaged by the face authentication camera 118 as the second information. Incidentally, the face authentication camera 118 is an example of means for imaging a face image of a user, a face image, which is imaged by other cameras (e.g., monitoring camera 116 or the like), may be acquired as the second information.
(Flow of Operation)

Next, flow of the operation of the information processing system 10 of the second embodiment will be described referring to FIG. 7. FIG. 7 is a flowchart showing the flow of the operation of the information processing system of the first embodiment. Incidentally, in FIG. 7, the same reference numeral is given to a processing, which is the same as the processing shown in FIG. 3.

Figure 7:
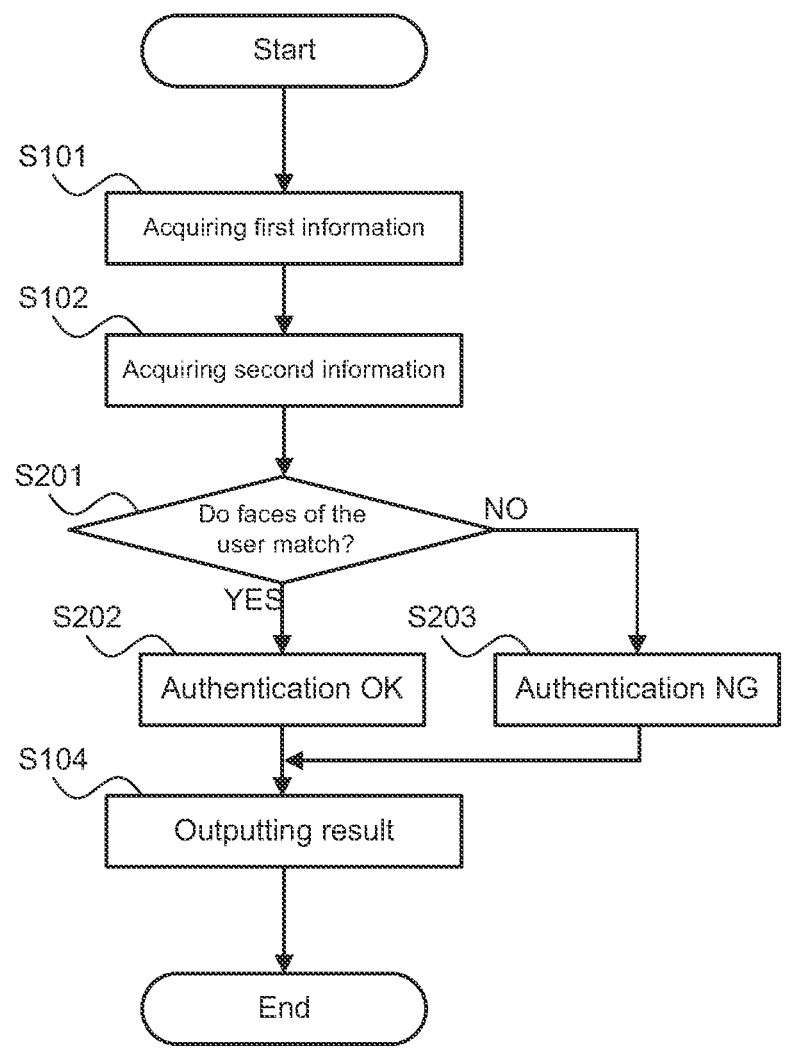
FIG. 7 is a flowchart showing flow of an operation of the information processing system of the second embodiment.

As shown in FIG. 7, when the information processing system 10 of the second embodiment operates, the first information acquiring unit 210 acquires the first information (step S101). The first information is associated with a face image of a user, who has gotten the specific inspection, for example. On the other hand, the second information acquiring unit 220 acquires the second information from the face authentication camera 118 (step S102). The second information is acquired as information including a face image of the user, as described above.

Subsequently, the determining unit 300 determines that whether or not the face of the user matches on the basis of the first information and the second information (step S201). Specifically, the determining unit 300 determines that whether or not the face image of the user associated with the first information (i.e., the face image of the user who has actually gotten the specific inspection) matches the face image acquired as the second information (i.e., the face image of the user who is the user of the system). Incidentally, since existing technologies are applied to the technique for determining of face matching, a detailed description thereof will be omitted.

When the face of the user of the first information and the face of the user of the second information are match each other (step S201: YES), the determining unit 300 determines that authentication of the user is successful (i.e., not spoofing) (step S202). On the other hand, when the face of the users of the first information and the face of the user of the second information do not match each other (step S201: NO), the determining unit 300 determines that authentication of the user is failure (i.e., there is a possibility of spoofing) (step S203). Then, the output unit 400 performs output according to the determination result of the determining unit 300 (step S104). For example, the output unit 400 allows the user to proceed with the procedure for entering to the country when it is determined that the authentication is successful. On the other hand, the output unit 400 may temporarily stop the procedure of the user for entering to the country, and output an alert to a system manager when the authentication is failure.
(Technical Effects)

Next, technical effects obtained by the information processing system 10 of the second embodiment will be described.

As described referring to FIGS. 6 and 7, in the information processing system 10 of the second embodiment, the determination is performed on the basis of the face image associated with the first information and the face image of the user acquired as the second information. In this way, it is possible to appropriately determine that whether or not the user has gotten the specific inspection (i.e., whether or not the user is spoofing other person, who has gotten the specific inspection).

Third Embodiment

The information processing system 10 of the third embodiment will be described referring to FIG. 8. Incidentally, the third embodiment is different from the first embodiment and the second embodiment described above in only a part of configuration and operation. Other part of the third embodiment may be the same as the first embodiment and the second embodiment. Therefore, in the following, portions overlapping with embodiments already described are appropriately omitted.
(Functional Configuration)

First, a functional configuration of the information processing system 10 of the third embodiment will be described referring to FIG. 8. FIG. 8 is a block diagram showing the functional configuration of the information processing system of the third embodiment. Incidentally, in FIG. 8, the same reference numeral is given to an element, which is the same as the component shown in FIG. 6.

Figure 8:
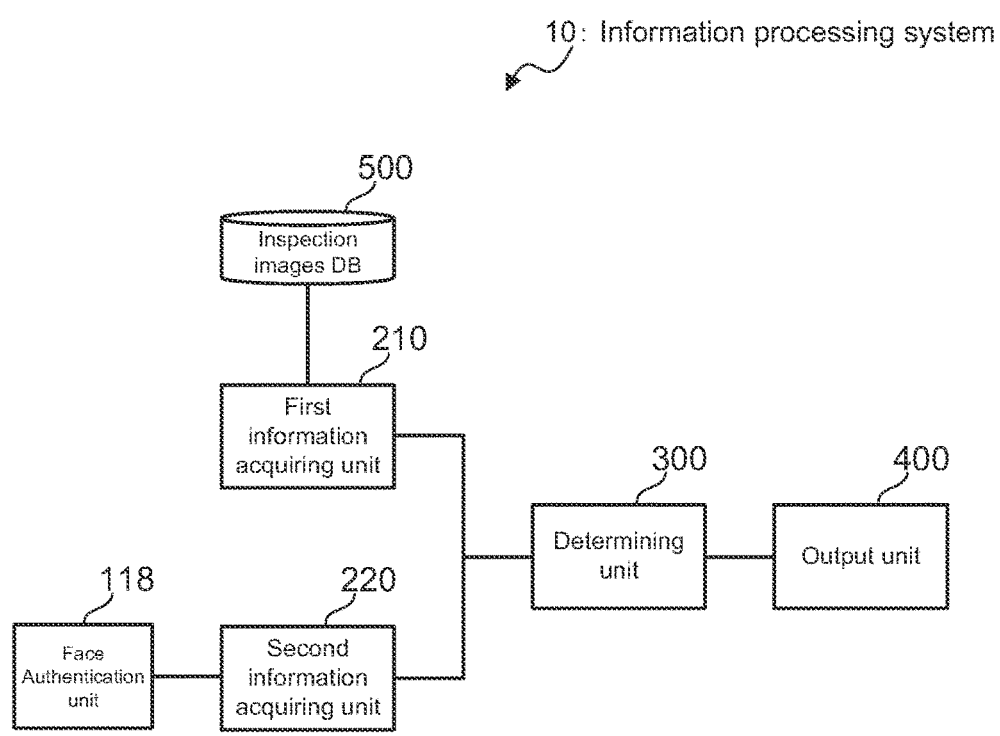
FIG. 8 is a block diagram showing a functional configuration of an information processing system of a third embodiment.

As shown in FIG. 8, the information processing system 10 of the third embodiment is configured to include the first information acquiring unit 210, the second information acquiring unit 220, the determining unit 300 and the output unit 400 as processing blocks for realizing the functions. In particular, the first information acquiring unit 220 of the third embodiment is configured to be able to read a face image of a user who has gotten the specific inspection from the inspection image database 500.

The inspection image database 500 is a database capable of storing face images of users, that are imaged at a venue of the specific inspection. Images stored in the inspection image database 500 are, in particular, a face image of a user in inspecting, or a face image of a user immediately after inspection. For example, the inspection image database 500 may store a face image of a user in a condition, in which a cotton swab for inspection is inserted into the user, and an image of a user at the moment of the injection (e.g., a condition, in which a needle is inserted into an arm). Alternatively, the inspection image database 500 may store a face image obtained by imaging a user immediately after completion of the inspection. In other words, the inspection image database 500 stores face images of users that are face images of users, from which it is known a user has gotten the inspection reliably. The inspection image database 500 may be constituted by the storage device 14 described above (see FIG. 1), for example.

(Technical Effects)

Next, technical effects obtained by the information processing system 10 of the third embodiment will be described.

As described referring to FIG. 8, in the information processing system 10 of the third embodiment, a face image of a user during inspection or immediately after inspection is associated with the first information. Images imaged in these condition can be images obtained by imaging the user, who has gotten the inspection reliably. Therefore, if the determination is performed by using these face images, it is possible to accurately determine that whether or not the user, who uses the system, is a user who has gotten the specific inspection.

Fourth Embodiment

The information processing system 10 of the fourth embodiment will be described referring to FIGS. 9 and 10. Incidentally, the fourth embodiment is different from the first to the third embodiments described above in only a part of configuration and operation. Other part of the fourth embodiment may be same as the first to the third embodiments. Accordingly, in the following, the description of the portions overlapping with the embodiments already described will be omitted as appropriate.

(Functional Configuration)

First, a functional configuration of the information processing system 10 of the fourth embodiment will be described referring to FIG. 9. FIG. 9 is a block diagram showing the functional configuration of the information processing system of the fourth embodiment. Incidentally, in FIG. 9, the same reference numeral is given to an element, which is the same as the component shown in FIG. 2.

Figure 9:
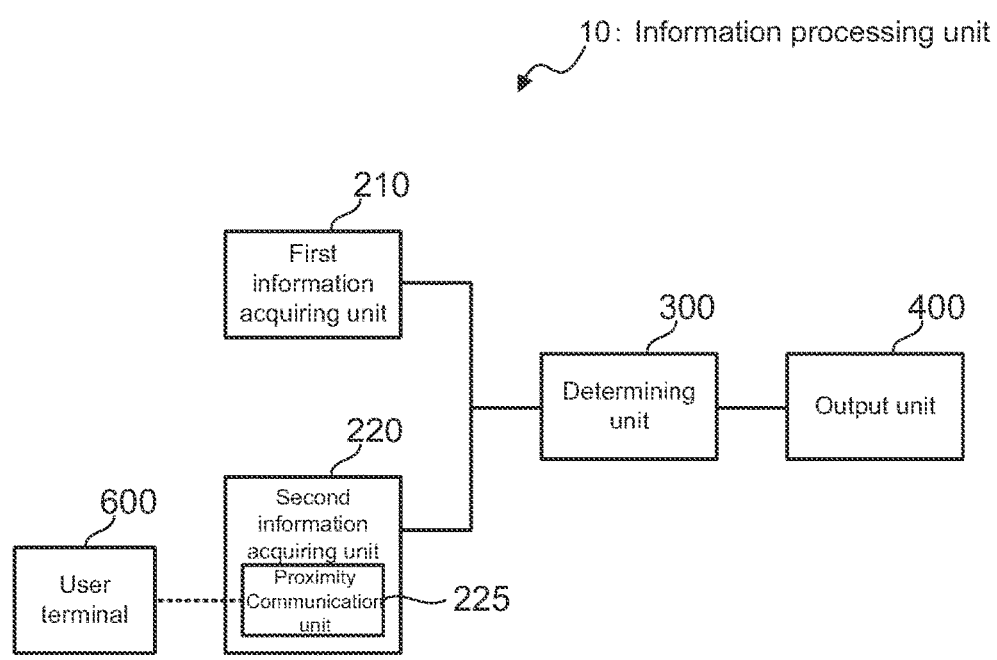
FIG. 9 is a block diagram showing a functional configuration of an information processing system of a fourth embodiment.

As shown in FIG. 9, the information processing system 10 of the fourth embodiment is configured to include the first information acquiring unit 210, the second information acquiring unit 220, the determining unit 300 and the output unit 400 as processing blocks for realizing the functions. In particular, the second information acquiring unit 220 of the fourth embodiment includes the proximity communication unit 225.

The proximity communication unit 225 is configured to be able to perform proximity communication with the user terminal 600 (e.g., a smartphone possessed by the user, etc.) existing in the vicinity. The proximity communication unit 225 is configured to be able to perform communication by Bluetooth (registered trademark), for example. The proximity communication unit 225 is configured to acquire information for identifying a user by proximity communication with the user terminal 600. The information for identifying the user may be personal information (e.g., a name, an address, a telephone number, or the like) of the user stored in the user terminal 600, or may be unique identification information of the user terminal 600.

(Flow of Operation)

Next, flow of the operation of the information processing system 10 of the fourth embodiment will be described referring to FIG. 10. FIG. 10 is a flowchart illustrating the flow of the operation of the information processing system of the fourth embodiment. Incidentally, in FIG. 10, the same reference numeral is given to a processing, which is the same as the processing shown in FIG. 3.

Figure 10:
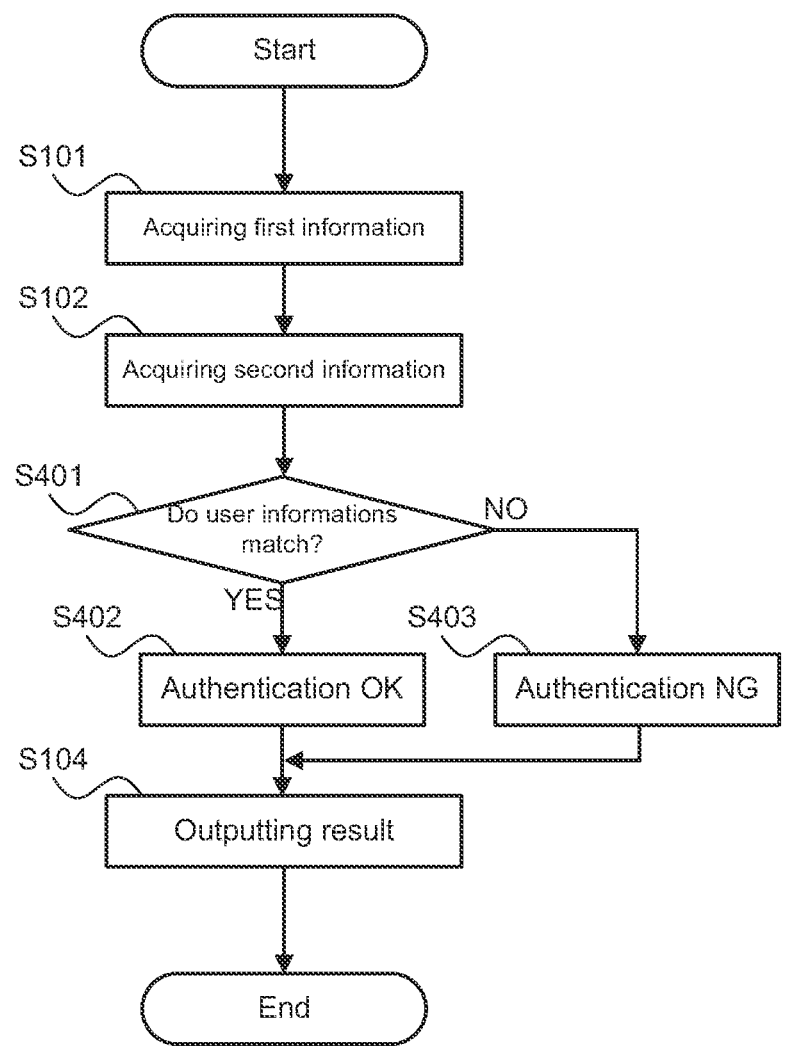
FIG. 10 is a flowchart showing flow of an operation of the information processing system of the fourth embodiment.

As shown in FIG. 10, when the information processing system 10 of the fourth embodiment operates, the first information acquiring unit 210 acquires the first information (step S10). Further, the second information acquiring unit 220 acquires the second information (step S102). The second information here, as already described, is acquired by proximity communication between the proximity communication unit 225 and the user terminal 600.

Subsequently, the determining unit 300 determines that whether or not the user information matches on the basis of the first information and the second information (step S401). Specifically, the determining unit 300 determines that whether or not the information of the user associated with the first information (i.e., the information of the user who has actually gotten the specific inspection) matches the information of the user acquired as the second information (i.e., the information acquired from the user terminal 600).

When the user information matches between the first information and the second information (step S401: YES), the determining unit 300 determines that the user authentication is successful (i.e., not spoofing) (step S402). On the other hand, when the user information does not match between the first information and the second information (step S401: NO), the determining unit 300 determines that authentication of the user is failure (i.e., there is a possibility of spoofing) (step S403). Then, the output unit 400 performs output according to the determination result of the determining unit 300 (step S104).

(Technical Effects)

Next, technical effects obtained by the information processing system 10 of the fourth embodiment will be described.

As described referring to FIGS. 9 and 10, in the information processing system 10 of the fourth embodiment, the determination is performed on the basis of the user information included in the first information and the second information acquired from the user terminal 600. In this way, it is possible to appropriately determine that whether or not the user has gotten the specific inspection (i.e., whether or not the user is spoofing other person, who has gotten the specific inspection).

Fifth Embodiment

The information processing system 10 of the fifth embodiment will be described referring to FIG. 11. Incidentally, the fifth embodiment is different from the first to the fourth embodiments described above in only a part of configuration and operation. Other part of the fifth embodiment may be the same as the first to the fourth embodiments. Accordingly, in the following, the description of the portions overlapping with the embodiments already described will be omitted as appropriate.

Concrete Example of the First Information

First, the first information acquired by the information processing apparatus 10 of the fifth embodiment will be described referring to FIG. 11. FIG. 11 is a table showing an example of the first information acquired by the information processing system of the fifth embodiment.

As shown in FIG. 11, the first information acquired by the information processing system 10 of the fifth embodiment includes information relating to name, result and date of the specific inspection. Further, the first information of the fifth embodiment in particular includes information relating to a plurality of types of inspections. The first information shown in FIG. 11 includes information relating to vaccination as the inspection (1). The first information includes information relating to PCR inspection as the inspection (2). Here, although an example in which the information of the two types of inspections are included in the first information, information relating to three or more inspections may be included.
(Technical Effects)

Next, technical effects obtained by the information processing system 10 of the fifth embodiment will be described.

As described referring to FIG. 11, in the information processing system 10 of the fifth embodiment, information relating to a plurality of types of specific inspections are included in the first information. In this way, it is possible to determine that whether or not the user has gotten a plurality of types of specific inspections (specifically, whether or not the user has gotten all of the plurality of types of specific inspections). Therefore, even when multiple types of specific inspection results are required in the entry inspection, for example, it is possible to provide information on each inspection.

Sixth Embodiment

The information processing system 10 of the sixth embodiment will be described referring to FIGS. 12 and 13. Incidentally, the sixth embodiment is different from the first to the fifth embodiments described above in only a part of configuration and operation. Other part of the sixth embodiment may be the same as the first to the fifth embodiments. Accordingly, in the following, the description of the portions overlapping with the embodiments already described will be omitted as appropriate.
(Functional Configuration)

First, a functional configuration of the information processing system 10 of to the sixth embodiment will be described referring to FIG. 12. FIG. 12 is a block diagram showing the functional configuration of the information processing system of the sixth embodiment. Incidentally, in FIG. 12, the same reference numeral is given to an element, which is the same as the component shown in FIG. 2.

Figure 12:
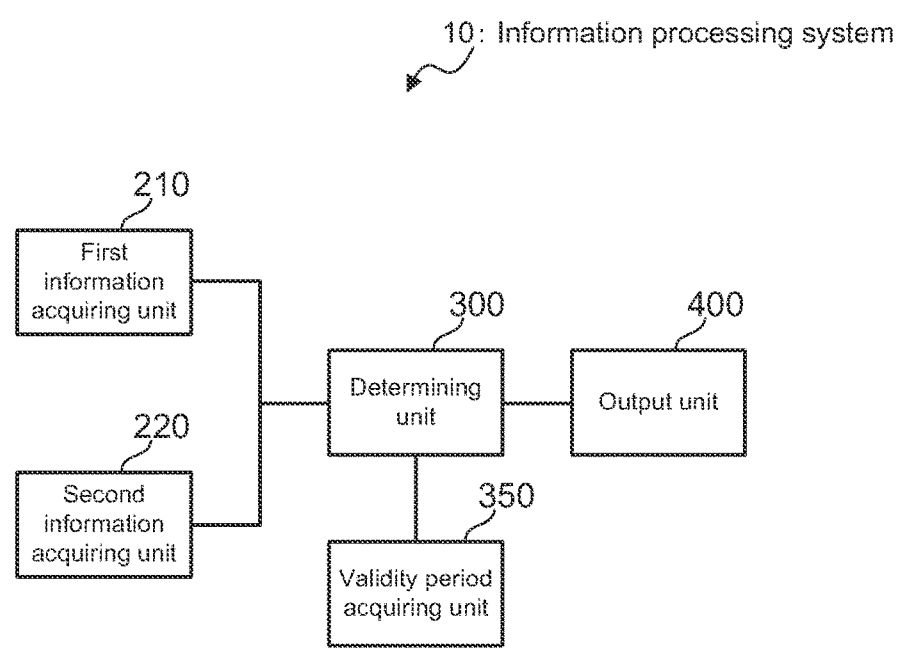
FIG. 12 is a block diagram showing a functional configuration of an information processing system of a sixth embodiment.

As shown in FIG. 12, the information processing system 10 of the sixth embodiment is configured to include the first information acquiring unit 210, the second information acquiring unit 220, the determining unit 300, the validity period acquiring unit 350 and the output unit 400 as processing blocks for realizing the functions. That is, the information processing system 10 of the sixth embodiment further comprises the validity period acquiring unit 350 in addition to the configuration of the first embodiment (see FIG. 2).

The validity period acquiring unit 350 is configured to be able to acquire information relating to the validity period for the specific inspection relating to the first information. The validity period may be a period, which is set in advance according to the characteristics of the inspection, for example. The validity period may be set to a different value for each inspection. The system is configured to output the information relating to the validity period acquired by the validity period acquiring unit 350 to the determining unit 300.

The determining unit 600 of the sixth embodiment is configured to perform a determination that whether or not the user has gotten the specific inspection in the validity period by using the first information acquired in the first information acquiring unit 210, and the information relating to the validity period acquired in the validity period acquiring unit 350. For example, if the validity period is two weeks, the determining unit 600 determines that whether or not the user has gotten the specific inspection in two weeks.
(Flow of Operation)

Next, flow of the operation of the information processing system 10 of the sixth embodiment will be described referring to FIG. 13. FIG. 13 is a flowchart showing the flow of the operation of the information processing system of the sixth embodiment. Incidentally, in FIG. 13, the same reference numeral is given to a processing, which is the same as the processing as shown in FIG. 3.

Figure 13:
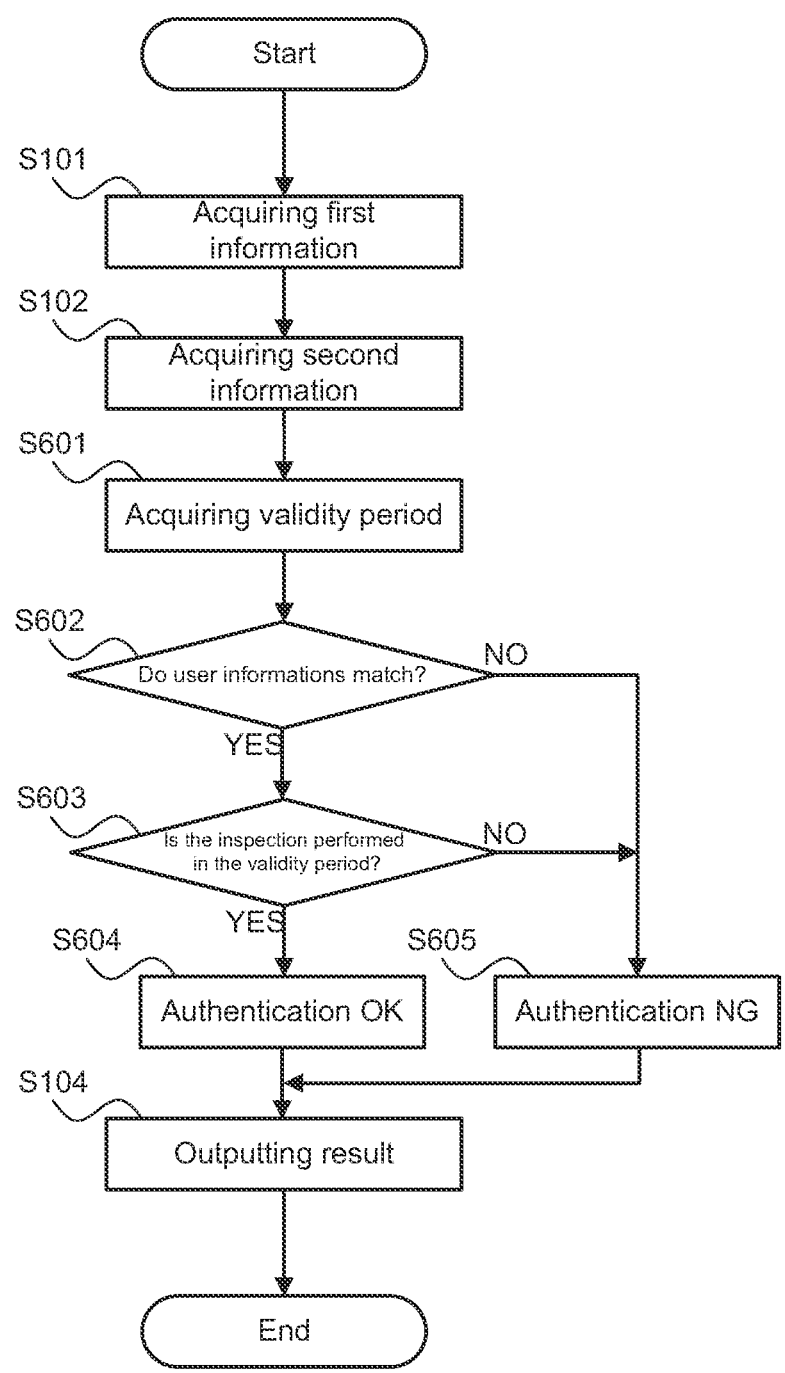
FIG. 13 is a flowchart showing flow of an operation of the information processing system of the sixth embodiment.

As shown in FIG. 13, when the information processing system 10 of the sixth embodiment operates, the first information acquiring unit 210 acquires the first information (step S101). The first information here includes information relating to date, in which an inspection is performed, as shown in FIG. 11, for example. On the other hand, the second information acquiring unit 220 acquires the second information (step S102).

Subsequently, in the sixth embodiment, in particular, the validity period acquiring unit 350 acquires information relating to the validity period (step S601). Incidentally, processing of the step S601 may be executed back and forth to each other with processing of the step S101 and the step S102 described above, or may be executed in parallel at the same time.

Subsequently, the determining unit 300 determines that whether or not the user information matches on the basis of the first information and the second information (step S602). When the user information matches in the first information and the second information (step S602: YES), the determining unit 300 further determines that whether or not the date, in which the specific inspection is performed, is in the validity period on the basis of the first information and the validity period information (step S603).

When the date, in which the specific inspection is performed, is within the validity period (step S603: YES), the determining unit 300 determines that the user's authentication is successful (i.e., not spoofing, and the inspection has been performed within the validity period) (step S604). On the other hand, when the user information does not match between the first information and the second information (step S602: NO), or when the date, in which the specific inspection is performed, is not in the validity period (step S603: NO), the determining unit 300 determines that the user's authentication is failure (i.e., there is a possibility of spoofing or the inspection has not been performed in the validity period) (step S605). Then, the output unit 400 performs output according to the determination result of the determining unit 300 (step S104).

(Technical Effects)

Next, technical effects obtained by the information processing system 10 of the sixth embodiment will be described.

As described referring to FIGS. 12 and 13, in the information processing system 10 of the sixth embodiment, it is determined that not only whether or not the user has gotten the specific inspection, but also whether or not the inspection has been performed within the validity period. In this way, it is possible not only to determine the spoofing of the user, it is possible to appropriately determine whether the inspection result is valid.

Seventh Embodiment

The information processing system 10 of the seventh embodiment will be described referring to FIGS. 14 and 15. Incidentally, the seventh embodiment is different from the first to the sixth embodiments described above in only a part of configuration and operation. Other part of the seventh embodiment may be the same as the first to the sixth embodiments. Accordingly, in the following, the description of the portions overlapping with the embodiments already described will be omitted as appropriate.

(Functional Configuration)

First, a functional configuration of the information processing system 10 of the seventh embodiment will be described referring to FIG. 14. FIG. 14 is a block diagram showing the functional configuration of the information processing system of the seventh embodiment. Incidentally, in FIG. 14, the same reference numeral is given to an element, which is the same as the component shown in FIG. 2.

Figure 14:
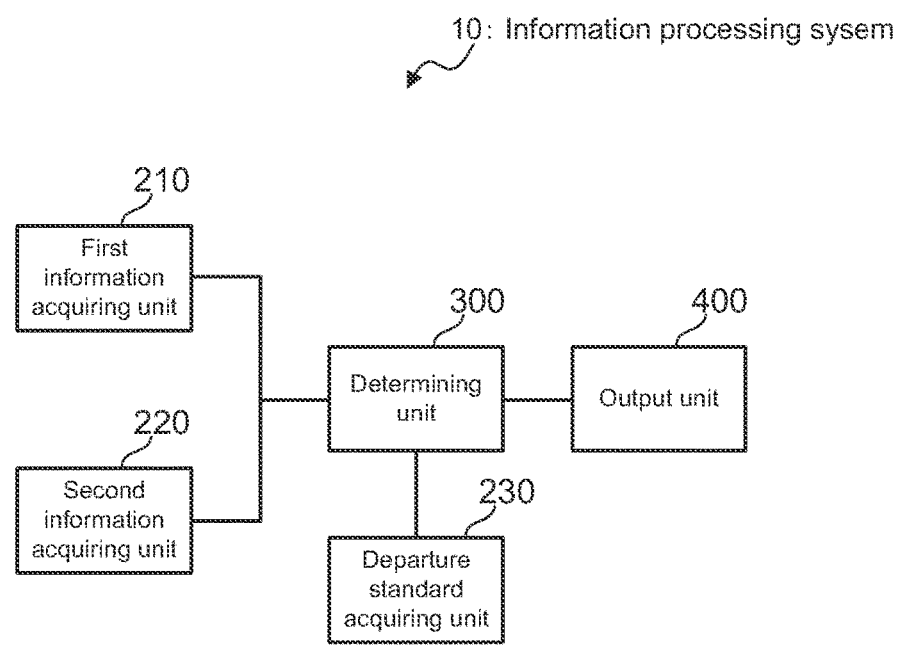
FIG. 14 is a block diagram showing a functional configuration of an information processing system of a seventh embodiment.

As shown in FIG. 14, the information processing system 10 of the seventh embodiment is configured to include the first information acquiring unit 210, the second information acquiring unit 220, the departure standard acquiring unit 230, the determining unit 300 and the output unit 400 as processing blocks for realizing the functions. That is, the information processing system 10 of the seventh embodiment further includes the departure standard acquiring unit 230 in addition to the configuration of the first embodiment (see FIG. 2).

The departure standard section 230 is configured to be able to acquire the information (third information) relating to the departure standard for the specific inspection. The departure standard is, for example, standard established for each country and may include, for example, condition for a type of a specific inspection and condition for when it was inspected. The system is configured to output the information relating to the departure standard acquired by the departure standard acquisition unit 230 to the determining unit 300.

The determining unit 300 of the seventh embodiment is configured to be able to perform the determination that whether or not a user meets the departure standard on the basis of the first information acquired by the first information acquiring unit 210 and the departure standard acquired by the departure standard acquiring unit 230. For example, if the departure standard conditions that "the Vaccine is inoculated within two months and the PCR inspection is gotten within one week and is negative", the determining unit 300 determines that whether or not the user is inoculated with the Vaccine within two months and whether or not the user has gotten the PCR inspection within one week and is negative.

(Flow of Operation)

Next, flow of the operation of the information processing system 10 of the seventh embodiment will be described referring to FIG. 15. FIG. 15 is a flowchart showing the flow of the operation of the information processing system of the seventh embodiment. Incidentally, in FIG. 15, the same reference numeral is given to a processing, which is the same as processing shown in FIG. 13.

Figure 15:
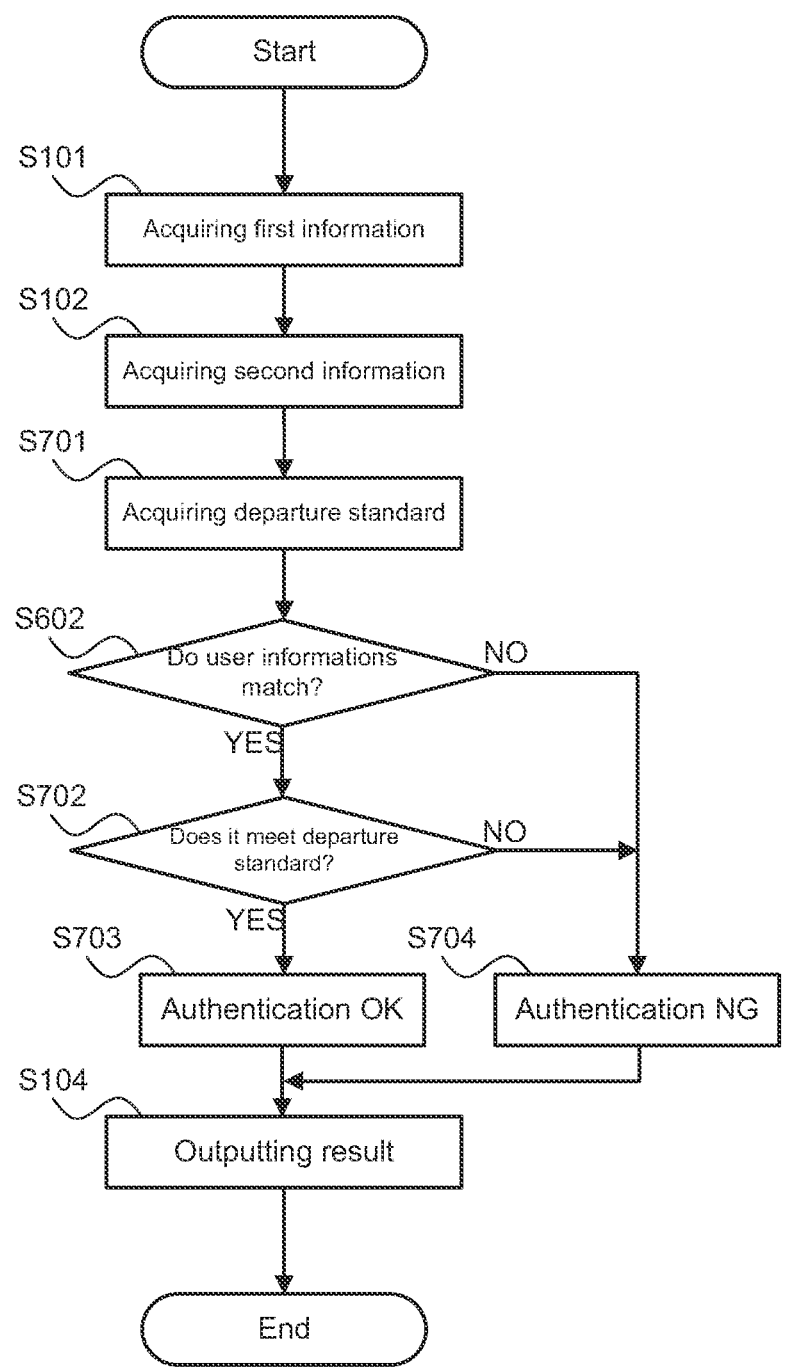
FIG. 15 is a flowchart showing flow of an operation of the information processing system of the seventh embodiment.

As shown in FIG. 15, when the information processing system 10 of the seventh embodiment operates, the first information acquiring unit 210 acquires the first information (step S101). The first information here includes information relating to the date, in which the inspection is performed, as shown in FIG. 11, for example. On the other hand, the second information acquiring unit 220 acquires the second information (step S102).

Subsequently, in the seventh embodiment, in particular, the departure standard acquiring unit 230 acquires information relating to the departure standard of the country from which the user intends to depart (step S701). Incidentally, processing of the step S701 may be executed back and forth to each other with processing of the step S101 and S102 described above, or may be executed in parallel at the same time.

Subsequently, the determining unit 300 determines that whether or not the user information matches on the basis of the first information and the second information (step S602). When the user information matches between the first information and the second information (step S602: YES), the determining unit 300 further determines that whether or not the user meets the departure standard on the basis of the first information and the third information (step S702).

When the user meets the departure standard (step S702: YES), the determining unit 300 determines that the user's authentication is successful (i.e., not spoofing, and meets the departure criteria) (step S703). On the other hand, when the user information does not match between the first information and the second information (step S602: NO), or when the user does not meet the departure standard (step S702: NO), the determining unit 300 determines that the user's authentication is failure (i.e., there is a possibility of spoofing, or the user does not meet the departure standard) (step S704). Then, the output unit 400 performs output according to the determination result of the determining unit 300 (step S104).

(Technical Effects)

Next, technical effects obtained by the information processing system 10 of the seventh embodiment will be described.

As described referring to FIGS. 14 and 15, in the information processing system 10 of the seventh embodiment, it is determined not only whether or not the user has gotten the specific inspection, but also whether or not the inspection has been performed so as to meet the departure standard. In this way, it is possible not only to determine the impersonation of the user but also to properly determine whether or not the user meets the departure standard. In the above-described embodiment, both the determination regarding spoofing and the determination regarding the departure standard are performed, however, only the determination regarding the departure standard may be performed without performing a determination regarding spoofing, for example.

Eighth Embodiment

The information processing system 10 of the eighth embodiment will be described referring to FIGS. 16 and 17. Incidentally, the information processing system 10 of the eighth embodiment is different from the first to the seventh embodiments described above in only a part of configuration and operation. Other part may be the same as the first to the seventh embodiments. Accordingly, in the following, the description of the portions overlapping with the embodiments already described will be omitted as appropriate.

(Functional Configuration)

First, a functional configuration of the information processing system 10 of the eighth embodiment will be described referring to FIG. 16. FIG. 16 is a block diagram showing the functional configuration of the information processing system of the eighth embodiment. Incidentally, in FIG. 16, the same reference numeral is given to an element, which is the same as the component shown in FIG. 2.

Figure 16:
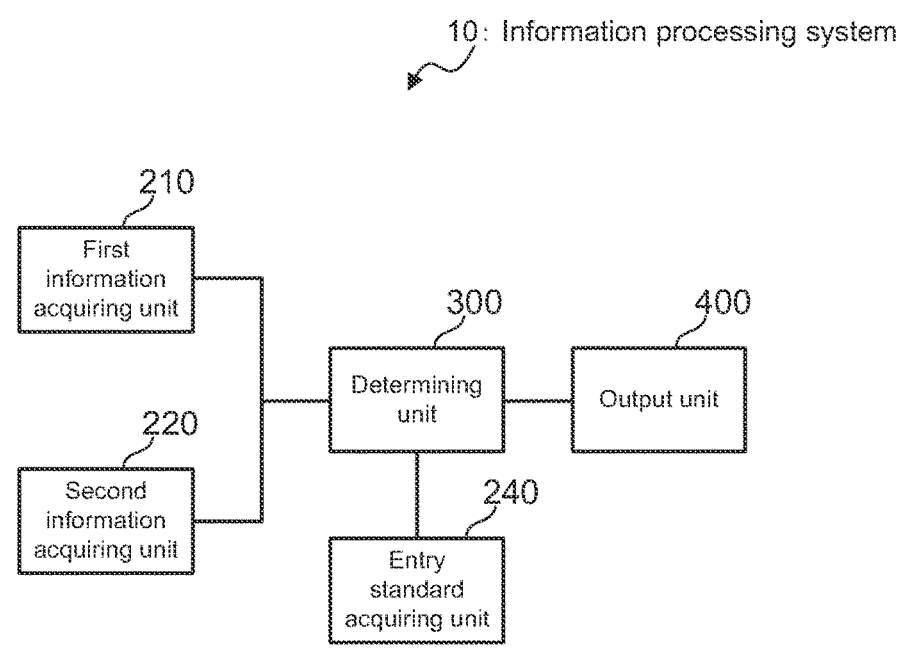
FIG. 16 is a block diagram showing a functional configuration of an information processing system of an eighth embodiment.

As shown in FIG. 16, the information processing system 10 of the eighth embodiment is configured to include the first information acquiring unit 210, the second information acquiring unit 220, the entry standard acquiring unit 240, the determining unit 300 and the output unit 400 as processing blocks for realizing the functions. That is, the information processing system 10 of the eighth embodiment further includes the entry standard acquiring unit 240 in addition to the configuration of the first embodiment (see FIG. 2).

The entry standard acquiring unit 240 is configured to acquire information (fourth information) relating to the entry standard for the specific inspection. The entry standard is, for example, standard established for each country and may include a condition for a type of specific inspection and a condition for when the inspection was taken. The system is configured to output the information relating to the entry standard acquired by the entry standard acquiring unit 240 to the determining unit 300.

The determining unit 300 of to the eighth embodiment is configured to perform the determination that whether or not a user meets the entry standard by using the first information acquired by the first information acquiring unit 210, and the entry standard acquired by the entry standard acquiring unit 240. For example, when the entry standard conditions that "the vaccine is inoculated within three months and the PCR inspection is gotten within two weeks and is negative", the determining unit 300 determines that whether or not the user is inoculated with the vaccine within three months, and whether or not the user has gotten the PCR inspection within two weeks and is negative.

(Flow of Operation)

Next, flow of the operation of the information processing system 10 of the eighth embodiment will be described referring to FIG. 17. FIG. 17 is a flowchart showing the flow of the operation of the information processing system of the eighth embodiment. Incidentally, in FIG. 17, the same reference numeral is given to a processing, which is the same as the processing shown in FIG. 3.

Figure 17:
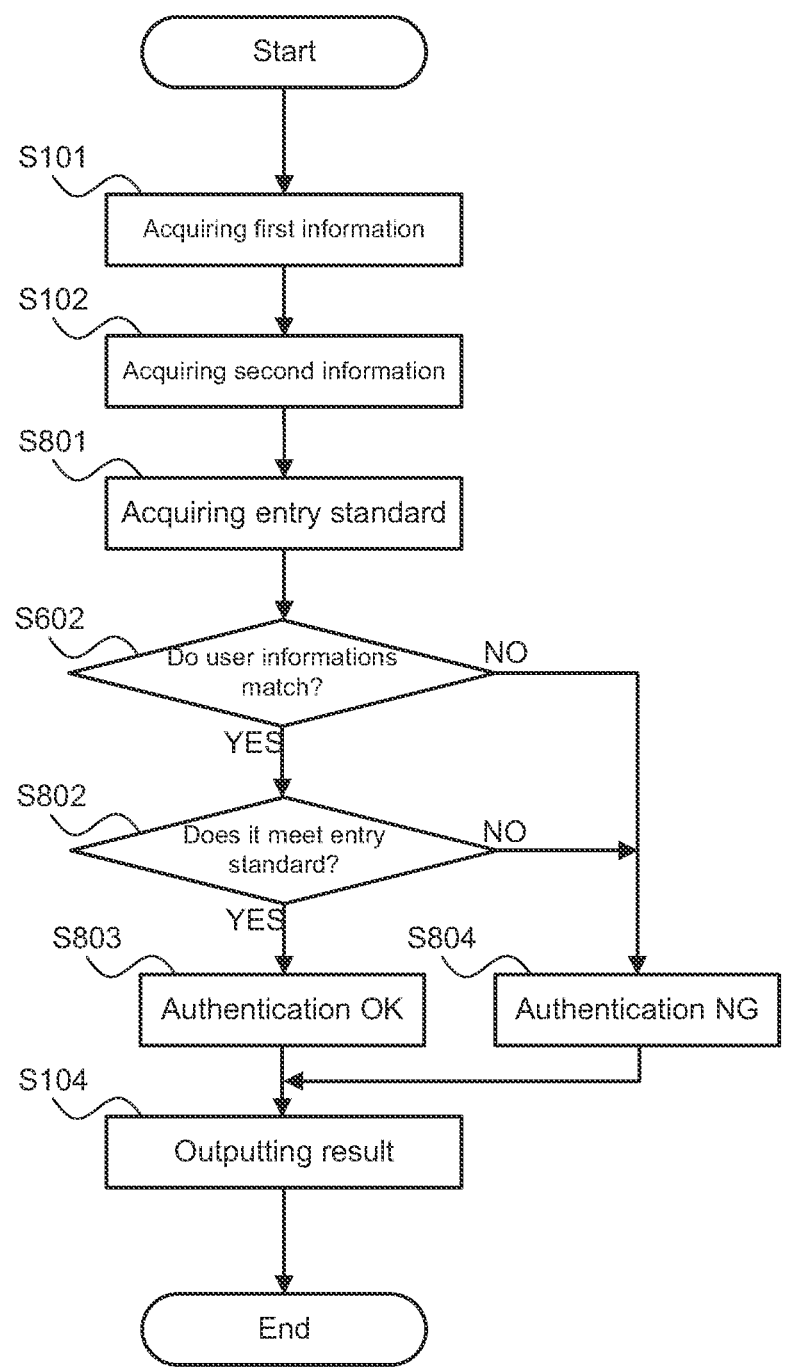
FIG. 17 is a flowchart showing flow of an operation of the information processing system of the eighth embodiment.

As shown in FIG. 17, when the information processing system 10 of the eighth embodiment operates, the first information acquiring unit 210 acquires the first information (step S101). The first information here includes information relating to the date, in which the inspection is performed, as shown in FIG. 11, for example. On the other hand, the second information acquiring unit 220 acquires the second information (step S102).

Subsequently, in the eighth embodiment, in particular, the entry standard acquiring unit 240 acquires information relating to the entry standard of the country, to which the user intends to enter (step S801). Incidentally, processing of the step S801 may be executed back and forth to each other with processing of the step S101 and the step S102 described above, or may be executed in parallel at the same time.

Subsequently, the determining unit 300 determines that whether or not the user information matches on the basis of the first information and the second information (step S602). When the user information matches between the first information and the second information (step S602: YES), the determining unit 300 further determines that whether or not the user meets the entry standard on the basis of the first information and the fourth information (step S802).

When the user meets the entry standard (step S802: YES), the determining unit 300 determines that the user's authentication is successful (i.e., not spoofing, and meets the entry standard) (step S803). On the other hand, when the user information does not match between the first information and the second information (step S602: NO), or when the user does not meet the entry standard (step S802: NO), the determining unit 300 determines that the user's authentication is failure (i.e., there is a possibility of spoofing or not meeting the entry standard) (step S804). Then, the output unit 400 performs output according to the determination result of the determining unit 300 (step S104).

(Technical Effects)

Next, technical effects obtained by the information processing system 10 of the eighth embodiment will be described.

As described referring to FIGS. 16 and 17, in the information processing system 10 of the eighth embodiment, it is determined not only whether or not the user has gotten the specific inspection, but also whether or not the inspection has been performed so as to meet the entry standard. In this way, it is possible not only to determine the impersonation of the user but also to properly determine whether or not the user meets the entry standard. In the above-described embodiment, both the determination regarding spoofing and the determination regarding the entry standard are performed, but for example, only the determination regarding the entry standard may be performed without performing the determination regarding spoofing.

Modification

Figure 18:
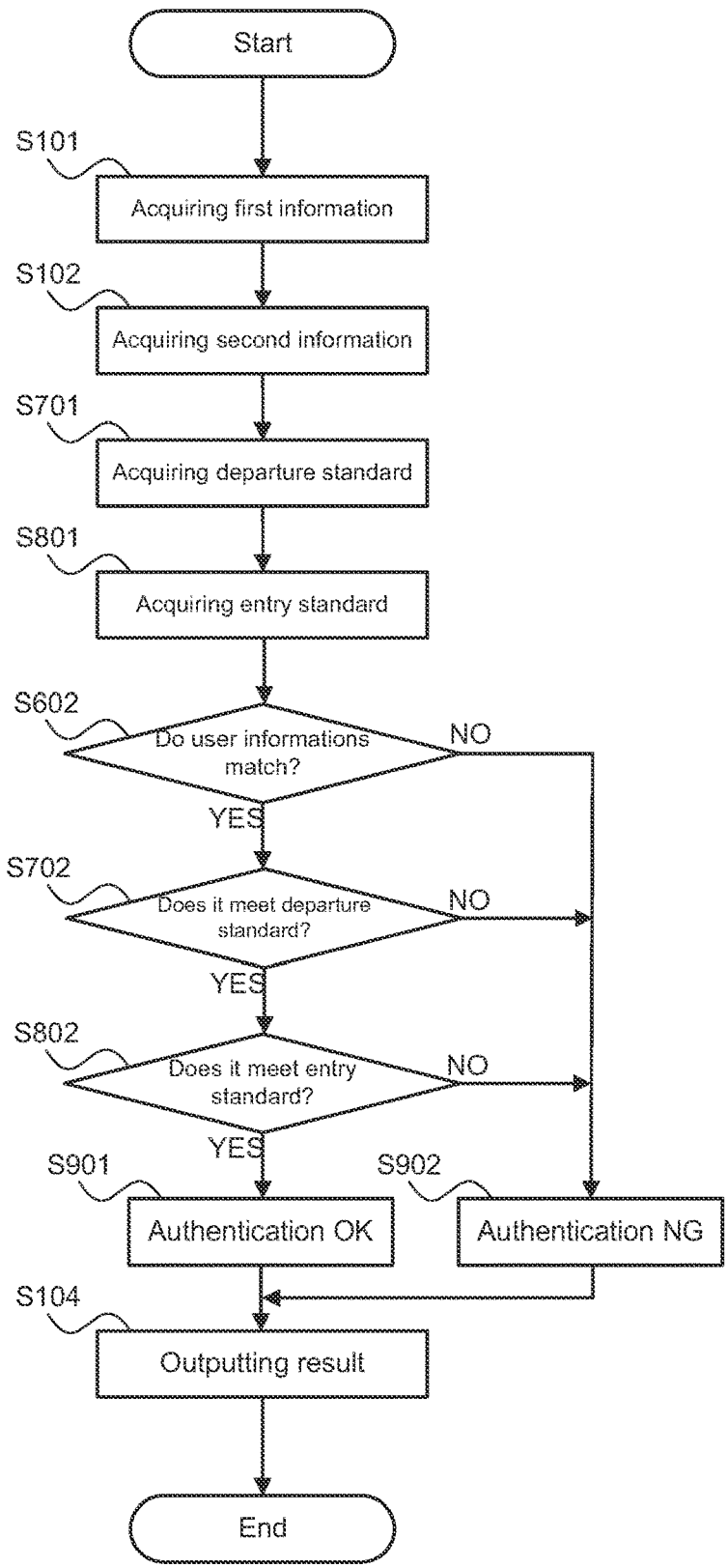
FIG. 18 is a flowchart showing flow of an operation of an information processing system of a modification of the eighth embodiment.

Next, a modification of the information processing system 10 of the eighth embodiment described above will be described referring to FIG. 18. FIG. 18 is a flowchart showing the flow of the operation of the information processing system of the modification of the eighth embodiment. Incidentally, it is assumed that the information processing system 10 of the modification is configured to include both the departure standard acquiring unit 230 described in the seventh embodiment, and the entry standard acquiring unit 240 described in the eighth embodiment.

As shown in FIG. 18, when the information processing system 10 of the modification operates, the first information acquiring unit 210 acquires the first information (step S101). The first information here includes information relating to the date, in which the inspection is performed as shown in FIG. 11, for example. On the other hand, the second information acquiring unit 220 acquires the second information (step S102).

Subsequently, in the modification, in particular, the departure standard acquiring unit 230 acquires information relating to the departure standard of the country, from which the user intends to depart (step S701). In addition, the entry standard acquiring unit 240 acquires information relating to the entry standard of the country, to which the user intends to enter after departure (step S801).

Subsequently, the determining unit 300 determines that whether or not the user information matches on the basis of the first information and the second information (step S602). When the user information matches between the first information and the second information (step S602: YES), the determining unit 300 further determines that whether or not the user meets the departure standard on the basis of the first information and the third information (step S702). Then, when the user meets the departure standard (step S702: YES), the determining unit 300 determines that whether or not the user meets the entry standard (step S802).

When the user meets the entry standard (step S802: YES), the determining unit 300 determines that the user's authentication is successful (i.e., not spoofing, and meets the departure and entry standards) (step S901). On the other hand, when the user information does not match between the first information and the second information (step S602: NO), when the user does not meet the departure standard (step S702: NO), or when the user does not meet the entry standard (step S802: NO), the determining unit 300 determines that the user's authentication is failure (i.e., there is a possibility of spoofing, or the user does not meet the departure standard or the entry standard) (step S902). Then, the output unit 400 performs output according to the determination result of the determining unit 300 (step S104).

As explained above, when the departure standard is set for the country, from which the user intends to depart, and the entry standard is set for the country, to which the user intends to enter after departure, the determination that whether or not the user meets the departure standard and the determination that whether or not the user meets the entry standard may be performed respectively at the timing of the user departure (i.e., during the departure examination).

A processing method, in which a program, which makes the configuration of each of embodiments described above operate so as to realize functions each of embodiments, is recorded on a recoding medium, and a computer executes the program by read the program recorded on the recoding medium as codes, is also included in the scope of each of embodiments. Therefore, a computer-readable recording medium is also included in range of each of embodiments. In addition, not only the recording medium on which the above-described program is recorded, but also the program itself is included in embodiments.

For example, a floppy (registered trademark) disk, a hard disk, an optical disk, a magnetic-optical disk, a CD-ROM, a magnetic tape, a non-volatile memory card or a ROM can be used as a recording medium. In addition, not only the program recorded on the recording medium itself is executed by processing, but also the program that operates on the operating system and executes processing in collaboration with other software and expansion board functions is included in the scope of the respective embodiments.

This disclosure can be modified as appropriate in range not contrary to range of the claim and the inventive summary or philosophy which can be read from the entire specification, and information processing systems, information processing methods, and computer programs with such modifications are also included in the technical philosophy of this disclosure.

<Supplementary Notes>

With respect to the embodiments described above, it may be further described as supplementary notes below, but is not limited to the following.

(Supplementary Note 1)

The information processing system according to supplementary note 1 is an information processing system comprising: a first acquiring means for acquiring a first information relating to performance of a specific inspection; a second acquiring means for acquiring a second information for determining that whether or not a user is a person who has gotten the specific inspection; a determining means for performing a determination that whether or not the user has gotten the specific inspection on the basis of the first information and the second information; and an output means for performing an output according to a result of the determination.

(Supplementary Note 2)

The information processing system according to supplementary note 2 is the information processing system according to supplementary note 1, wherein the second information includes a face image of the user, and the determining means performs the determination that whether or not the user has gotten the specific inspection on the basis of the face image of the user and a face image associated with the first information.

(Supplementary Note 3)

The information processing system according to supplementary note 3 is the information processing system according to supplementary note 2, wherein the face image associated with the first information is an image which has been imaged during of immediately after the performance of the specific inspection.

(Supplementary Note 4)

The information processing system according to supplementary note 4 is the information processing system according to any one of supplementary notes 1 to 3, wherein the second acquiring means acquires at least a part of the second information by proximity communication with a terminal possessed by the user.

(Supplementary Note 5)

The information processing system according to supplementary note 5 is the information processing system according to any one of supplementary notes 1 to 4, wherein the specific inspection includes a plurality of types of inspections.

(Supplementary Note 6)

The information processing system according to supplementary note 6 is the information processing system of any one of supplementary notes 1 to 5, wherein the first information includes information about time in which the specific inspection is performed, and the determining means performs the determination that whether or not the user has gotten the specific inspection in a predetermined period.

(Supplementary Note 7)

The information processing system according to supplementary note 7 is the information processing system according to any one of supplementary notes 1 to 6, wherein the information processing system further comprises a third acquiring means for acquiring a third information relating to a departure standard of a country from which the user intends to depart, and the determining means performs the determination that whether or not the user has gotten the specified inspection so that the user meets the departure standard on the basis of the first information, the second information and the third information.

(Supplementary Note 8)

The information processing system according to supplementary note 8 is the information processing system according to any one of supplementary notes 1 to 7, wherein the information processing system further comprises a fourth acquiring means for acquiring fourth information relating to an entry standard, and the determining means performs the determination that whether or not the user has gotten the specified inspection so that the user meets the entry standard on the basis of the first information, the second information and the fourth information.

(Supplementary Note 9)

The information processing method according to supplementary note 9 is an information processing method comprising: acquiring a first information relating to performance of a specific inspection; acquiring a second information for determining the whether or not a user is a person who has gotten the specific inspection; determining that whether or not the user has gotten the specific inspection on the basis of the first information and the second information; and performing an output according to the result of the determination.

(Supplementary Note 10)

The computer program described according to supplementary note 10 is a computer program causing a computer to: acquiring a first information relating to performance of a specific inspection; acquiring a second information for determining the whether or not a user is a person who has gotten the specific inspection; determining that whether or not the user has gotten the specific inspection on the basis of the first information and the second information; and performing an output according to the result of the determination.

(Supplementary Note 11)

The recording medium according to supplementary note 11 is a recording medium recording the computer program according to supplementary note 10.

DESCRIPTION OF REFERENCE NUMERALS AND LETTERS

10 Information processing system
11 Processor
100 Operation terminal
118 Face authentication camera
210 First information acquiring unit
220 Second information acquiring unit
225 Proximity communication unit
230 Departure standard acquiring unit
240 Entry standard acquiring unit
300 Determining unit
350 Validity period acquiring unit
400 Output unit
500 Inspection image database
600 User terminal

What is claimed is:

1. An information processing system comprising:
at least one memory configured to store instructions; and
at least one processor configured to execute the instructions to:
acquire a first information relating to performance of a specific inspection;
acquire a second information for determining that whether or not a user is a person who has gotten the specific inspection;
perform a determination that whether or not the user has gotten the specific inspection based on the first information and the second information; and
perform an output according to a result of the determination,
wherein the first information includes information about a time in which the specific inspection is performed, and
wherein the at least one processor is further configured to execute the instructions to perform the determination that whether or not the user has gotten the specific inspection in a predetermined period, wherein the predetermined period is a period set in advance according to a characteristic of the specific inspection.

2. The information processing system according to claim 1, wherein
the second information includes a face image of the user, and
the at least one processor is configured to execute the instructions to perform the determination that whether or not the user has gotten the specific inspection based on the face image of the user and a face image associated with the first information.

3. The information processing system according to claim 2, wherein the face image associated with the first information is an image which has been imaged during of immediately after the performance of the specific inspection.

4. The information processing system according to claim 2, wherein the at least one processor is configured to execute the instructions to acquire at least a part of the second information by proximity communication with a terminal possessed by the user.

5. The information processing system according to claim 2, wherein the specific inspection includes a plurality of types of inspections.

6. The information processing system according to claim 2, wherein the at least one processor is configured to execute the instructions to:
acquire a third information relating to a departure standard of a country from which the user intends to depart, and
perform the determination that whether or not the user has gotten the specific inspection so that the user meets the departure standard based on the first information, the second information and the third information.

7. The information processing system according to claim 3, wherein the at least one processor is configured to execute the instructions to acquire at least a part of the second information by proximity communication with a terminal possessed by the user.

8. The information processing system according to claim 3, wherein the specific inspection includes a plurality of types of inspections.

9. The information processing system according to claim 1, wherein the at least one processor is configured to execute the instructions to acquire at least a part of the second information by proximity communication with a terminal possessed by the user.

10. The information processing system according to claim 9, wherein the specific inspection includes a plurality of types of inspections.

11. The information processing system according to claim 1, wherein the specific inspection includes a plurality of types of inspections.

12. The information processing system according to claim 2, wherein the at least one processor is configured to execute the instructions to:
acquire a third information relating to a departure standard of a country from which the user intends to depart, and perform the determination that whether or not the user has gotten the specific inspection so that the user meets the departure standard based on the first information, the second information and the third information.

13. The information processing system according to claim 1, wherein the at least one processor is configured to execute the instructions to:
acquire fourth information relating to an entry standard, and
perform the determination that whether or not the user has gotten the specific inspection so that the user meets the entry standard based on the first information, the second information and the fourth information.

14. An information processing method comprising:
acquiring a first information relating to performance of a specific inspection;
acquiring a second information for determining the whether or not a user is a person who has gotten the specific inspection;
determining whether or not the user has gotten the specific inspection based on the first information and the second information; and
performing an output according to a result of the determining,
wherein the first information includes information about a time in which the specific inspection is performed, and
wherein the determining comprises determining whether or not the user has gotten the specific inspection in a predetermined period, wherein the predetermined period is a period set in advance according to a characteristic of the specific inspection.

15. A non-transitory recording medium on which a computer program is recorded, the computer program causing a computer to:
acquiring a first information relating to performance of a specific inspection;
acquiring a second information for determining the whether or not a user is a person who has gotten the specific inspection;
determining whether or not the user has gotten the specific inspection based on the first information and the second information; and
performing an output according to a result of the determining,
wherein the first information includes information about a time in which the specific inspection is performed, and
wherein the determining comprises determining whether or not the user has gotten the specific inspection in a predetermined period, wherein the predetermined period is a period set in advance according to a characteristic of the specific inspection.

* * * * *